United States Patent [19]

Ristimaki et al.

[11] Patent Number: 4,920,727

[45] Date of Patent: May 1, 1990

[54] CASSETTE SYSTEM AND APPARATUS FOR MANUFACTURING AN ACTIVE AGENT LIBERATING CAPSULE FOR SUBCUTANEOUS USE

[75] Inventors: Mikko V. Ristimaki, Nouoiainen; Matti J. Lehtinen, Kaarina; Krister J. Lindstrom; Rolf R. Hartzell, both of Turku, all of Finland

[73] Assignee: Huhtamaki Oy, Finland

[21] Appl. No.: 289,711

[22] Filed: Dec. 27, 1988

[30] Foreign Application Priority Data

Dec. 30, 1987 [FI] Finland .................................. 875762

[51] Int. Cl.$^5$ ......................... B65B 1/04; B29C 39/18
[52] U.S. Cl. ...................................... 53/252; 29/433;
53/236; 425/90; 425/110; 425/164; 425/512
[58] Field of Search .................. 53/296, 500, 266 R, 53/522, 558, 512, 252, 236, 500, 558; 29/231, 433, 467; 425/110, 289, 90, 97, 445, 446, 506, 508, 510, 517, 512, 142, 115, 163, 164

[56] References Cited

U.S. PATENT DOCUMENTS

| | | | |
|---|---|---|---|
| 3,256,674 | 6/1966 | Rutherford | 53/522 |
| 3,545,168 | 12/1970 | Day | 53/266 |
| 3,669,309 | 6/1972 | Romeo | 53/522 |
| 4,341,728 | 7/1982 | Robertson et al. | 264/161 |
| 4,453,368 | 6/1984 | Egee | 53/252 |

Primary Examiner—Willard Hoag
Attorney, Agent, or Firm—Lalos & Keegan

[57] ABSTRACT

The invention relates to a cassette system for inserting a rod inside a tubular basic element. The system consists of at least two elongated plate-shaped cassettes provided with transverse channels as well as of a shank whereby the rods placed in channels of one cassette can be pushed into the tubular basic elements placed in channels of the other cassette after placing the cassettes in alignment with each other. The invention relates also to an apparatus for manufacturing a subcutaneous prophylactic capsule, comprising a tubular basic element and a hormone rod placed therein. The apparatus comprises a first conveyor for carrying an empty cassette one step forward in cooperation with a tube advancing and cutting means, a second conveyor for carrying a filled tube cassette to a swelling bath and then to a hormone rod insertion spot, a third conveyor for carrying hormone capsule alongside tube cassette to insertion spot as well as a pusher means whose shanks insert the hormone rods into the tubes placed in channels of tube cassette, a fourth conveyor for carrying tube cassette to drying, a capsule switching station for advancing the capsules to a glueing capsule so that the ends of said capsules project on either side of a cassette, said ends being glued and sealed in a glueing assembly as well as a cutting means for cutting the capsule.

7 Claims, 4 Drawing Sheets

CASSETTE SYSTEM AND APPARATUS FOR MANUFACTURING AN ACTIVE AGENT LIBERATING CAPSULE FOR SUBCUTANEOUS USE

The present invention relates to a cassette system and an apparatus whereby it is possible to manufacture an active agent containig capsules for subcutaneous use. Such capsules are described for example in U.S. Pat. No. 3 854 480 and consist of a fluid-permeable tubing, generally a silicone tubing, inside which is inserted a rod containing a hormone substance and the ends of said tubing are sealed. This prophylactic capsule is placed under the skin and the hormones are liberated due to solubility and diffusion processes. This way the capsule works for years and is very simple to use.

These kinds of capsules are well suited for administering small amounts of active agent for a longer period. Hormones are especially suitable for use in such capsules, but of course any kind of active agent with suitable properties can be used.

Manufacturing of a capsule according to the afore said is however time-consuming and has been done heretofore manually, particularly inconvenient is the insertion of an active agent containing rod in a polymer tubing. The insertion of such a rod in a polymer tubing is even as such a difficult manual operation but, in addition to this, care must be taken that the rod is properly placed in a polymer tubing so that the ends of a tubing can be readily sealed.

U.S. Pat. No. 4,341,728 and the corresponding Finnish Patent Application No. 814088, inventors Dale N. Robertson and John Braun, discloses a method for manufacturing an intrauterine prophylactic capsule containing a medical substance. In this prior known apparatus, polymer mass containing a medical substance is formed into suitably shaped rod elements in a multicavity mould. After the moulding, the elements are removed and cut which is not, however, described in more detail. According to the cited Specification, the release rate of a medical substance can be decelerated and structure of the apparatus can be reinforced by pulling a medicine-permeable tube over the medicine tubing. How this is performed has not been described.

An object of the present invention is to provide a cassette system and a manufacturing apparatus which employs the system and whereby subcutaneous active agents liberating capsules can be produced in larger quantities effectively and without impairing the quality of the end product.

A cassette system of the invention is characterized in that said system includes at least two elongated plate-shaped cassettes provided with channels extending transversely of the cassette and parallel to each other for a tubular basic element or a rod as well as a shank-shaped pusher for inserting the rods placed in the channels of a cassette inside the tubular basic elements placed in the channels of a cassette and, if necessary, the basic elements carrying said rods can be pushed out of the cassette into a third cassette, which pushing motion is effected after placing the cassettes side by side and the channels in alignment with each other.

In a cassette intended for the basic element said channels are preferably open upwards. This has been accomplished by means of a groove above the channels, said groove extending from the top surface of a cassette all the way to the channel. Thus, fluid can be readily evaporated from the surface of a basic element.

When handling the cassettes it is preferable to employ a retaining means for holding the basic elements in the channels.

This is why the grooves of a cassette for the basic element are provided with recesses through which the retaining means can be pushed into contact with pieces of tubing in the channel.

In view of the use of a cassette, it is important that the cooperating cassettes can be aligned precisely side by side and in a manner that the channels of the cassettes are exactly in alignment with each other. This is why the cassettes are provided with alignment holes in the ends thereof.

The invention relates also to an apparatus utilizing the above-described cassettes. An apparatus of the invention for manufacturing subcutaneous prophylactic capsules is characterized in that said apparatus comrises filling station, a drying station and a glueing and final flushing station, said filling station comprising:

a first conveyor which catches an empty tubing cassette and carries it one step forward in cooperation with a tubing advancing and cutting means, a second conveyor which carries a tubing cassette, with pieces of tubing inserted in its channels, into a swelling bath and further to a hormone rod filing insertion point, a third conveyor which carries a hormone casette provided with hormone rods alongside said tubing cassette to insertion spot with channels of the cassettes in alignment and a pusher cooperating with third conveyor and which pusher after the insertion of a hormone capsule is moving towards the hormone capsule in the direction of its channels, whereby shanks corresponding to the number and position of the channels in said casettes penetrate into channels of hormone casette for inserting the hormone rods into the tubes in the tubing cassette whereby said pusher, after a pushing motion is completed, moves away from cassettes to a rest position, said third conveyor being further adapted to carry an empty hormone casette into a casette storage , a fourth conveyor which carries a tubing cassette provided with pieces of tubing or capsules filled with hormone rods to a predrying step and on to a following drying means, a capsule switching station, wherein the capsules are moved by means of a pusher into a glueing capsule whose width is less than the length of the capsules so that both ends of the capsules project on either side of a cassette, a glueing means for glueing the projecting ends of a capsule simultaneously or periodically, said apparatus further including a cutting means for cutting a capsule to a desired length and/or a flushing and washing device.

Thus, an apparatus of the invention consists of a plurality of individual sections in cooperation with each other. The cooperation of these individual sections is preferably controlled by a computer for as precise an operation as possible and for high capacity.

Other characterizing features of the invention are set forth in the annexed claims.

An embodiment of this invention, the manufacture of a hormone containing capsules for prophylactic use, is described in more detail with reference to the accompaying drawing. It should, however, be noted that hormones and the prophylactic use are just examples of utilizing the invention.

BRIEF DESCRIPTION OF THE DRAWINGS

FIG. 1 shows the operating principle for a cassette system of the invention and FIGS. 2 and 3 show the cassettes employed.

FIG. 2 shows a so-called tubing cassette, comprising a plate element 1 provided with parallel channels 2 extending transversely of the longitudinal direction of a cassette. The top portion of these channels 2 is provided with grooves 3, having inclined walls and running parallel to the channels and extending from the top surface of a cassette to the top surface of a channel 2. This provides an open channel 2. In each groove 3, within the central area of a cassette, the wall surface is provided with a hole-like recess 4 for a retaining means. Along the short side of a cassette, adjacent to its end, there are two holes 5 for a catching means.

FIG. 3 shows a cassette assembly intended for cooperation with a tubing cassette shown in FIG. 2. A cassette, or a hormone capsule, shown in FIG. 3 comprises a capsule similar to that shown in FIG. 2 but the hormone capsule is only provided with channels 7 extending through the cassette as well as with pairs of holes 5 intended for a catching means and positioned along the short sides of a cassette 6, adjacent to its edge.

Figure 3:
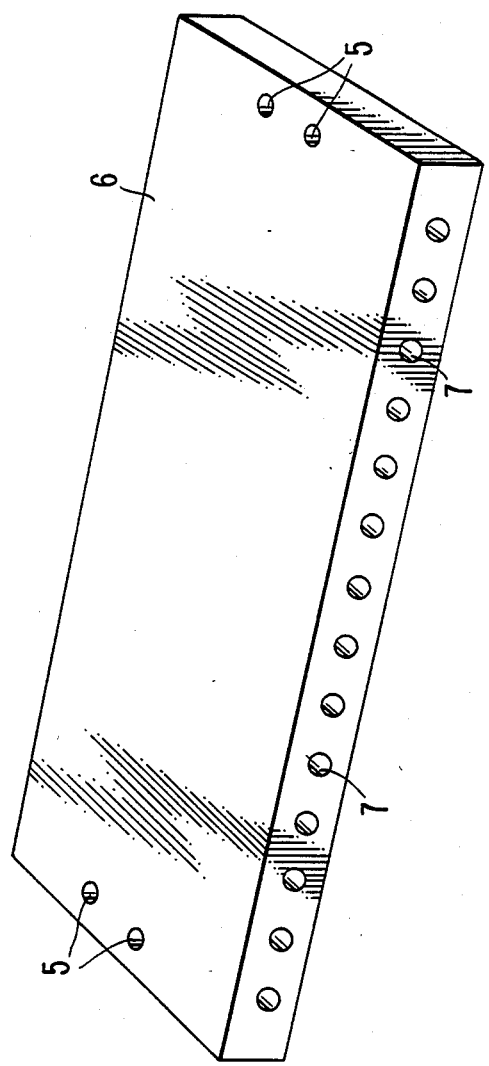
FIG. 3 shows a medicine cassette according to the invention.

Employed in the invention is still a third cassette whose structure in principle is similar to a hormone capsule shown in FIG. 3 except that this third cassette is narrower than the hormone capsule so that the ends of said hormone capsule on either side remain outside the cassette for glueing the ends.

Figure 1:
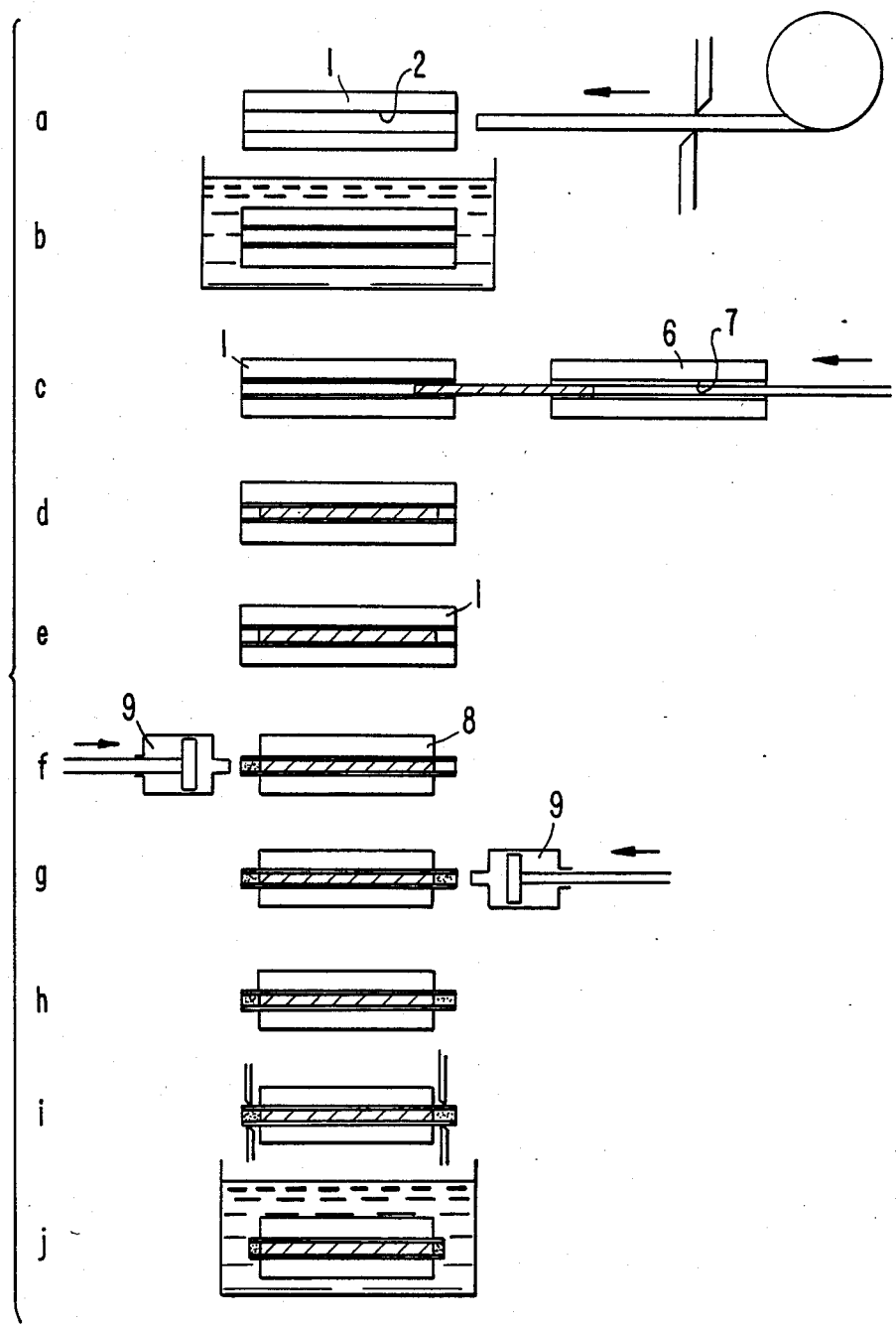
FIG. 1 shows the operating principle for cassettes of the invention.

FIG. 1 shows in principle the use of capsules of the invention, A supply roller is used to advance a polymer tubing to a cutting means for cutting the polymer tubings into suitable lengths. These severed tube lengths are inserted into a first channel 2 in cassette 1. As an alternative, it is of course possible to insert the tubing into first channel 2 and to cut it as it is in position. Thereafter, cassette 1 advances a step and another length of tubing is inserted into the next channel 2. When all channels 2 are filled with tubings, cassette 1 advances from a first handling step (a) to a next handling step (b) which comprises a swelling path. The conveyor carries cassette 1 with its polymer tubing to point (b) and dips the cassette in a swelling bath followed by withdrawing the cassette from the bath, whereafter the swelling fluid is drained out and the cassette carried to a next working station (c) for bringing alongside cassette 1 a hormone capsule 6 carrying as many hormone capsule rods as polymer tube cassette 1 as polymer tubings in channels 2. The channels 7 of a hormone cassette are positioned exactly so as to match the positions of channels 2 in cassette 1. The cassettes are aligned alongside each other and shanks are inserted into each channel 7 from outside said hormone capsule 6. Thus, the hormone rods placed in channels 7 eject out of capsule 6 and directly into the polymer tubings placed in channels 2 of cassette 1. After the polymer tubing is filled with hormone rods, said cassette 1 is predried at step (d). A step (e) comprises final drying. Thereafter, cassette 1 together with its filled tubings is shifted alongside a glueing cassette 8 and both cassettes 1 and 8 are aligned so that their channels will be in register with each other. Then, a tubing with its hormone rod is pushed out of a tube cassette into a glueing cassette so that a portion of both ends of the capsule remains outside cassette 8. The ends are glued at steps (f) and (g). In FIG. 1, the glueing is effected in two steps but obviously it can also be effected in a single step, i.e. both ends of a cassette are glued in the same step. Since the hormone rod inserted in a polymer tubing is shorter than the polymer tubing itself, there will be a small empty space remaining at the ends of a tubing. This empty space is filled with glue by means of adhesive-supply pumps 9. Following the adhesive supply, a glued capsule is dried at a step (h), whereafter the excessive ends of a capsule are removed by cutting. This is followed by washing and rinsing a capsule and cassette at a step (j). According to the figure, this is effected by dipping cassette 1 in rinsing fluid. In principle, rinsing and washing can be effected in several steps and for example in a manner that the capsules have been removed from a cassette. Rinsing can also be supplemented by a sterilization step.

Thus, FIG. 1 illustrates in principle the operation of a cassette system of the invention.

Figure 4:
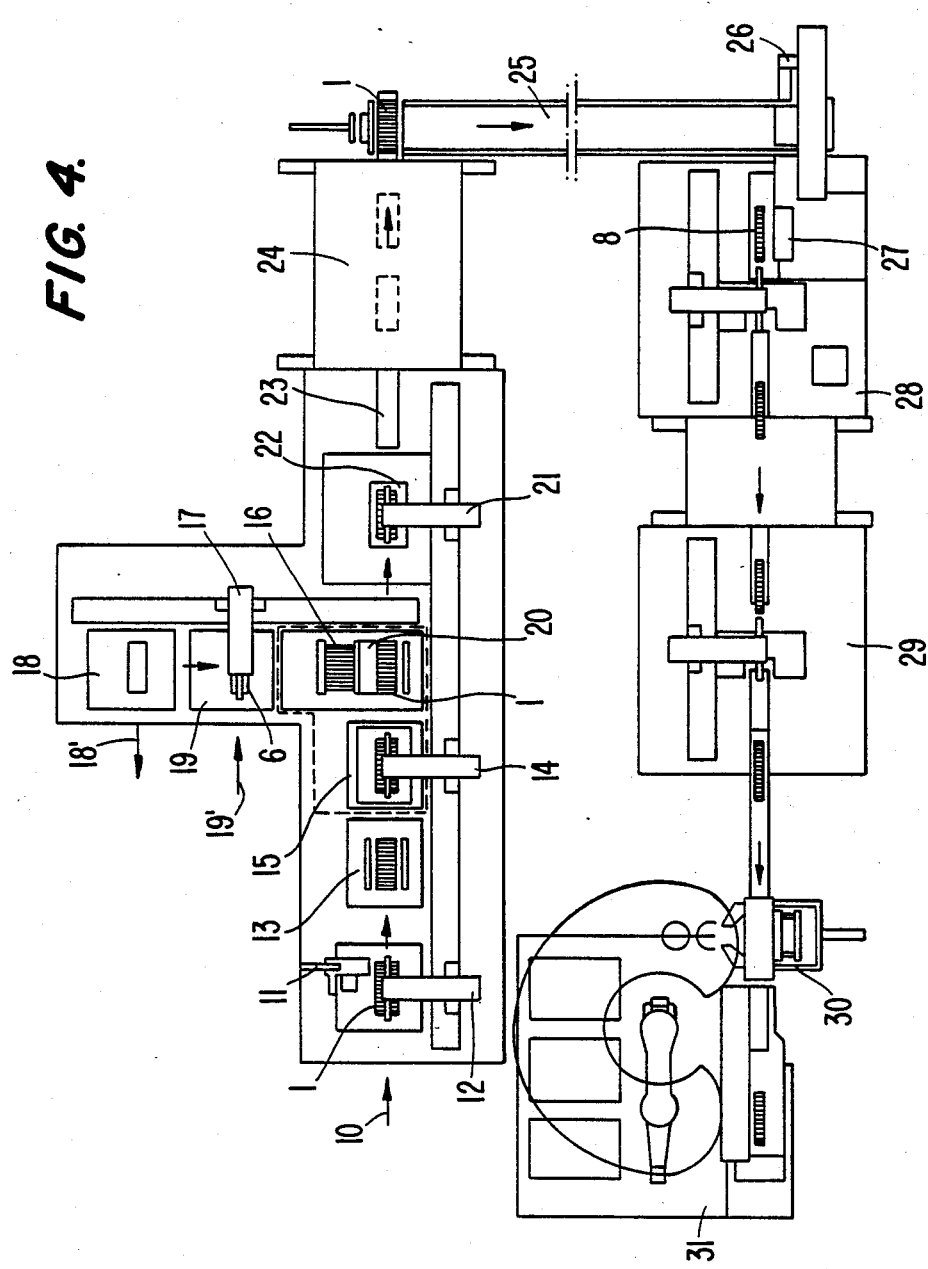
FIG. 4 shows an apparatus of the invention for manufacturing a hormone capsule.

FIG. 4 shows an apparatus of the invention for manufacturing a capsule containing a hormone medicine and consisting of polymer tubing by using a cassette system of the invention.

Figure 2:
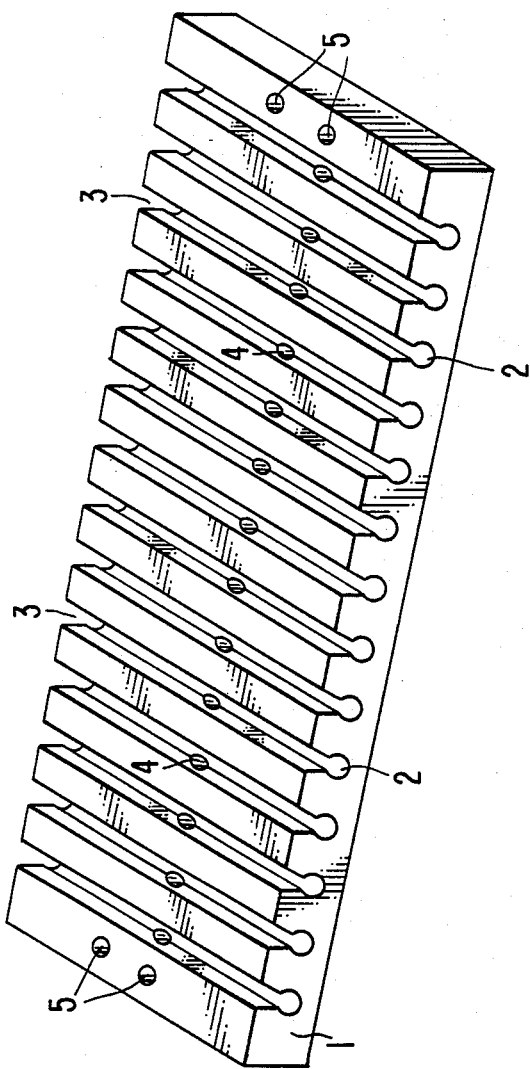
FIG. 2 shows a tubing cassette employed in the invention.

At an arrow indicated by numeral 10, the forward end of an apparatus is supplied with cassettes 1 shown in the canted FIG. 2. This cassette supply at the forward end of an apparatus is fitted with a lift mechanism which takes a pile of cassettes upward brining the top cassette 1 to flush with the top level of the apparatus. In this position, a conveyor 12 catches the cassette by means of gripper-like catching members and catching holes 5 provided in the cassette to carry cassette 1 to a starting position. A supply reel 11 unwinds polymer tubing working its way into a first channel 2 in cassette 1. The polymer tubing consists of silicone tubing, preferably dimethyl siloxane. After inserting it into first channel 2, the tubing is severed with a cutting means and conveyor 12 carries cassette 1 one step forward whereby the next channel 2 positions itself in front of a tube supply mechanism and the next length of tubing is advanced into the empty channel 2. This operation continues until all channels 2 in cassette 1 are filled with tubes. Thereafter, conveyor 12 carries a filled cassette 1 to a leveling station 13 and leaves it there. Conveyor 12 returns to the starting position and catches a cassette 1 on top of the pile of cassettes and its filling proceeds as described above.

Towards the longitudinal edges of a cassette 1 at leveling station 13 are urged levelling means, whereby the lengths of tubing possibly projecting from a cassette are pushed in and the tubes are leveled in cassette 1. To a leveled or trimmed cassette 1 is now brought a conveyor 14 which engages this cassette with catching means. Conveyor 14 is further fitted with a comb means consisting of a row of shanks between the catching means. These shanks penetrate into holes 4 in cassette 1 in contact with the tubings placed in channels 2. Cassette 1 is carried away from leveling station 13, said conveyor 14 at the same time turning the cassette from horizontal position to vertical position and lowering the cassette into a swelling bath 15. After the swelling bath treatment, conveyor 14 carries cassette 1 to the next working step for filling cassette 1 with hormone rods. However, prior to filling, excess of swelling liquid is removed from said cassette 1, which removal being enhanced by grooves 3 on the top surface of a cassette through which the swelling fluid, which is cyclohexane, can easily evaporate. A cassette 1 filled with swelled silicone tubes is laid on a base so that one of its longitudinal sides comes against an abutment. At the opposite longitudinal side of a cassette there is a vacant space 20 wherein a conveyor 17 brings a hormone cassette 6 immediately adjacent to the cassette.

A hormone cassette 6 is shown in FIG. 3. It resembles a polymer tube cassette but does not include evaporation grooves 3. In addition, this cassette 6 is narrower than cassette 1. A pile of such hormone cassettes 6, into whose channels 7 have been inserted hormone rods previously, are placed in a hormone capsule filling station 19 at a location shown by an arrow 19'. This filling station is also provided with a lift mechanism so that the top cassette rises to the operating level of the apparatus. Here a conveyor means 17 picks up to the top cassette by means of gripper-like catching members and engagement holes 5 and carries it to said vacant spot 20 alongside cassette 1. The cassettes are aligned in register with each other in a manenr that channels 2, 7 of both cassettes are in alignment with each other. Thereafter, the shanks 16 on the side of hormone cassette 6 opposite to tube cassette 1, the number and position of said shanks matching channels 7 of hormone casettes 6, are inserted into these channels. The movement of shanks 16 results in that the hormone rods placed in channels 7 of hormone casette 6 are pushed out of the casette and into the polymer tubes in channels 2 of casette 1. In order to hold polymer tubes more effectively, it is possible to apply pressure or compression. An abutment at the opposite longitudinal edge of cassette 1 prevents the polymer tubes from pushing out of a cassette and the hormone rods from penetrating too far. When all hormone rods are inserted into the tubes in casette 1, said shank means 16 is retracted and conveyor 17 advances to an unloading station 18 for empty hormone casette 6 from which the piled-up hormone casettes are discharged at an arrow 18'. After the unloading, said conveyor 17 returns to filling station 19 and catches the following hormone casette.

After the filling, casette 1 is carried by means of a conveyor 21 to a predrying step 22 for a treatment lasting appr. 15 minutes. From here said conveyor 21 carries casette 1 onto a belt conveyor 23 of a drying tower 24. The final drying of a capsule is effected in the drying tower in circa 60 minutes and at a temperature of 50° C.

A cassette 1 thus dried is carried by a transverse conveyor 25 to a glueing step. At the rearward end of transverse conveyor 25 a conveyor 26, whose construction resembles the conveyors used at the forward end of the apparatus, carries cassette 1 to a station 27 for placing cassette 1 alongside a glueing cassette 8. The transfer of casettes from one cassette to another is effected by applying the same technique as in the insertion of hormone rods into cassette 1.

The structure of a glueing cassette corresponds to that of hormone cassette 6 although the glueing cassette is narrower, so that both ends of a polymer tube inserted therein project out of the capsule on either side by circa 6 mm. A thus filled adhesive cassette 6 is carried to the glueing station which in FIG. 4 is shown as a two-step design, there are two glueing stations 28 and 29.

Since a hormone rod inserted in a polymer tube is shorter than the polymer tube, a small void will be formed at each end of the polymer tube corresponding substantially to that portion of a polymer tube which projects out of each longitudinal side of an adhesive cassette. In the glueing operation, into each of a tube is inserted an adhesive injector for filling this void with glue. In FIGS. 1 and 4, this glueing is effected in two steps. Naturally, the glueing can also be effected also in a single step, whereby on either side of an adhesive cassette the adhesive injectors are simultaneously aligned with the capsules. Furthermore, the glueing can be effected by glueing all capsules at the same time; by glueing at the same time all capsule ends facing in the same direction or by effecting the glueing with one capsule at a time, the conveyor advancing the cassette stepwise one capsule at a time to align with an adhesive injector for glueing. After the drying, an adhesive cassette is carried to a cutting means 30 for removing the extra ends of a capsule. The cutting means 30 is also accompanied by a washing and rinsing assembly 31 which, in the case of FIG. 4, is provided with three different rinsing tanks. In the embodiment shown in FIG. 4, the cassette is carried by a conveyor from one rinsing tank to the next and the rinsed cassette is carried to an exit. The rinsing can of course be effected also in the cassette or capsules can be removed from the cassette and rinsed freely for example in a basket designed for this purpose.

After such rinsing and drying the capsules are ready for packaging.

I claim:

1. An apparatus for manufacturing a subcutaneous prophylactic capsule, having a tubular fluid-permeable basic element, and a hormone rod inserted therein, said apparatus comprising a tubing cassette, a filling means, a drying means as well as a glueing and final rinsing means, said filling means further comprising, a first conveyor with means for catching an empty tubing cassette and carrying it one step forward and a tubing advancing and cutting means, a second conveyor for carrying said tubing cassette, with pieces of tubing inserted in its channels, associated with a swelling bath and a hormone rod insertion means, a third conveyor a hormone cassette, for carrying said hormone cassette provided with hormone rods alongside said tubing cassette to insertion means with channels of the cassettes in alignment, and a pusher cooperating with said third conveyor and which pusher after the insertion of a hormone capsule is movable towards the hormone capsule in the direction of its channels, whereby shanks corresponding to the number and position of the channels in said cassettes penetrate into channels of hormone cassette for inserting the hormone rods into the tubes in the tubing cassette whereby said pusher, after a pushing motion is completed, being movable away from cassettes to a rest position, said third conveyor being further positioned to carry an empty hormone cassette into a cassette storage means, a fourth conveyor, a predrying means and drying means positioned relative said fourth conveyor such that the fourth conveyor can carry a tubing cassette filled with hormone rods or capsules sequentially to aid predrying means and said drying means.

a capsule switching means, wherein the capsules are movable by means of a pusher into a glueing cassette whose width is less than the length of the capsules so that both ends of the capsules project on either side of cassette, a glueing means for glueing the projecting ends of a capsule simultaneously or periodically, said apparatus further including a cutting means for cutting a capsule to a desired length and a rinsing and washing assembly.

2. A conveyor as set forth in claim 1 including being fitted with retaining means which penetrate into recesses of cassette.

3. An apparatus as set forth in claim 2, wherein said glueing means comprises an adhesive injector for injecting glue into cavities at both open ends of a capsule.

4. An apparatus as set forth in claim 1, including a computer-control means for controlling the cooperation of individual components in the apparatus.

5. An apparatus as set forth in claim 1 or 4, wherein said glueing means comprises an adhesive injector for injecting glue into cavities at both open ends of a capsule.

6. An apparatus as set forth in claim 1 or 4, wherein said second conveyor is fitted with a swinging mechanism for turning the cassette from a horizontal position to a vertical position relative to channels, in which position the cassette is dipped in a swelling bath.

7. An apparatus as set forth in claim 6, wherein said glueing means comprises an adhesive injector for injecting glue into cavities at both open ends of a capsule.

* * * * *